(12) United States Patent
Mahadevan et al.

(10) Patent No.: US 12,180,318 B2
(45) Date of Patent: Dec. 31, 2024

(54) IMIDAZOLIUM ZWITTERION POLYMERIZABLE COMPOUNDS AND OPHTHALMIC DEVICES INCORPORATING THEM

(71) Applicant: Johnson & Johnson Vision Care, Inc., Jacksonville, FL (US)

(72) Inventors: Shivkumar Mahadevan, Jacksonville, FL (US); Dola Sinha, Jacksonville, FL (US); Yong Zhang, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 713 days.

(21) Appl. No.: 17/317,259

(22) Filed: May 11, 2021

(65) Prior Publication Data

US 2021/0388141 A1 Dec. 16, 2021

Related U.S. Application Data

(60) Provisional application No. 63/039,485, filed on Jun. 16, 2020.

(51) Int. Cl.
*C08F 283/12* (2006.01)
*A61F 2/16* (2006.01)
*C07D 233/64* (2006.01)
*G02B 1/04* (2006.01)

(52) U.S. Cl.
CPC ............. *C08F 283/12* (2013.01); *A61F 2/16* (2013.01); *C07D 233/64* (2013.01); *G02B 1/043* (2013.01)

(58) Field of Classification Search
CPC .................................................. G02B 1/043
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 3,808,178 A | 4/1974 | Gaylord |
| 4,113,224 A | 9/1978 | Clark et al. |
| 4,120,570 A | 10/1978 | Gaylord |
| 4,136,250 A | 1/1979 | Mueller et al. |
| 4,153,641 A | 5/1979 | Deichert et al. |
| 4,197,266 A | 4/1980 | Clark et al. |
| 4,436,887 A | 3/1984 | Chromecek et al. |
| 4,495,313 A | 1/1985 | Larsen |
| 4,659,782 A | 4/1987 | Spinelli |
| 4,659,783 A | 4/1987 | Spinelli |
| 4,691,820 A | 9/1987 | Martinez |
| 4,740,533 A | 4/1988 | Su et al. |
| 4,889,664 A | 12/1989 | Kindt-Larsen et al. |
| 4,906,623 A * | 3/1990 | Matsumura .......... C07D 501/46 514/202 |
| 4,910,277 A | 3/1990 | Bambury et al. |
| 5,006,622 A | 4/1991 | Kunzler et al. |
| 5,034,461 A | 7/1991 | Lai et al. |
| 5,039,459 A | 8/1991 | Kindt-Larsen et al. |
| 5,054,610 A | 10/1991 | Ajello |
| 5,070,215 A | 12/1991 | Bambury et al. |
| 5,236,969 A | 8/1993 | Kunzler et al. |
| 5,244,981 A | 9/1993 | Seidner et al. |
| 5,270,418 A | 12/1993 | Kunzler et al. |
| 5,298,533 A | 3/1994 | Nandu et al. |
| 5,314,960 A | 5/1994 | Spinelli et al. |
| 5,331,067 A | 7/1994 | Seidner et al. |
| 5,337,888 A | 8/1994 | Morrison |
| 5,371,147 A | 12/1994 | Spinelli et al. |
| 5,375,698 A | 12/1994 | Ewart et al. |
| 5,409,104 A | 4/1995 | Lovell |
| 5,467,868 A | 11/1995 | Abrams et al. |
| 5,515,964 A | 5/1996 | Bauman |
| 5,573,108 A | 11/1996 | Hamilton et al. |
| 5,609,246 A | 3/1997 | Borghorst et al. |
| 5,695,049 A | 12/1997 | Bauman |
| 5,697,495 A | 12/1997 | Abrams et al. |

(Continued)

FOREIGN PATENT DOCUMENTS

| | | |
|---|---|---|
| CN | 107118300 A | 9/2017 |
| EP | 0080539 B1 | 6/1983 |

(Continued)

OTHER PUBLICATIONS

Kitagawa (JP 5560637) English machine translation (Year: 2014).*
Compendium of Polymer Terminology and Nomenclature: IUPAC Recommendations 2008, edited by: Richard G. Jones, Jaroslav Kahovec, Robert Stepto, Edward S. Wilks, Michael Hess, Tatsuki Kitayama, and W. Val Metanomski.
Crivello, et al, Photoinitiators for Free Radical Cationic & Anionic Photopolymerisation, 2nd Edition, vol. III, pp. 275-298, John Wiley and Sons, New York, 1998.
Vijayakrishna et al, Polymeric Vesicles and Micelles Obtained by Self-Assembly of Ionic Liquid-Based Block Copolymers Triggered by Anion or Solvent Exchange, Macromolecules, 2009, vol. 42, pp. 5167-5174.
Vijayakrishna et al, Synthesis by RAFT and Ionic Responsiveness of Double Hydrophilic Block Copolymers Based on Ionic Liquid Monomer Units, Macromolecules, 2008, vol. 41, pp. 6299-6308.

(Continued)

*Primary Examiner* — Michael F Pepitone
(74) *Attorney, Agent, or Firm* — Raef M. Shaltout

(57) ABSTRACT

Provided are imidazolium zwitterion polymerizable compounds and their applications in ophthalmic devices and packaging solutions. The zwitterionic polymerizable compounds are of formula I:

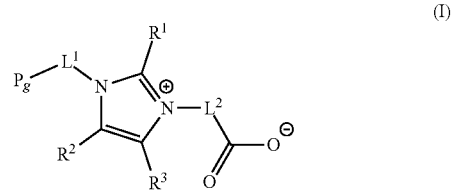

wherein $R^1$, $R^2$, $R^3$, $L^1$, $L^2$, and $P_g$ are as described herein.

18 Claims, No Drawings

(56) References Cited

U.S. PATENT DOCUMENTS

| | | |
|---|---|---|
| 5,704,468 A | 1/1998 | Lust et al. |
| 5,711,416 A | 1/1998 | Bauman |
| 5,722,536 A | 3/1998 | Pierce et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,823,327 A | 10/1998 | Wu et al. |
| 5,824,719 A | 10/1998 | Kunzler et al. |
| 5,849,811 A | 12/1998 | Nicolson et al. |
| 5,962,548 A | 10/1999 | Vanderlaan et al. |
| 5,965,631 A | 10/1999 | Nicolson et al. |
| 5,983,608 A | 11/1999 | Wu et al. |
| 5,998,498 A | 12/1999 | Vanderlaan et al. |
| 6,020,445 A | 2/2000 | Vanderlaan et al. |
| 6,029,808 A | 2/2000 | Peck et al. |
| 6,044,966 A | 4/2000 | Haase |
| 6,087,415 A | 7/2000 | Vanderlaan et al. |
| 6,367,929 B1 | 4/2002 | Maiden et al. |
| 6,401,915 B1 | 6/2002 | Faxe |
| 6,420,453 B1 | 7/2002 | Bowers et al. |
| 6,423,761 B1 | 7/2002 | Bowers et al. |
| 6,767,979 B1 | 7/2004 | Muir et al. |
| 6,822,016 B2 | 11/2004 | McCabe et al. |
| 6,867,245 B2 | 3/2005 | Iwata et al. |
| 6,943,203 B2 | 9/2005 | Vanderlaan et al. |
| 6,951,894 B1 | 10/2005 | Nicolson et al. |
| 7,052,131 B2 | 5/2006 | McCabe et al. |
| 7,247,692 B2 | 7/2007 | Laredo |
| 7,249,848 B2 | 7/2007 | Laredo et al. |
| 7,396,890 B2 | 7/2008 | Zanini et al. |
| 7,461,937 B2 | 12/2008 | STeffen et al. |
| 7,468,398 B2 | 12/2008 | Nicolson et al. |
| 7,538,146 B2 | 5/2009 | Nicolson et al. |
| 7,553,880 B2 | 6/2009 | Nicolson et al. |
| 7,572,841 B2 | 8/2009 | Chen et al. |
| 7,666,921 B2 | 2/2010 | McCabe et al. |
| 7,691,916 B2 | 4/2010 | McCabe et al. |
| 7,786,185 B2 | 8/2010 | Rathore et al. |
| 7,825,170 B2 | 11/2010 | Steffen et al. |
| 7,915,323 B2 | 3/2011 | Awasthi et al. |
| 7,934,830 B2 | 5/2011 | Blackwell et al. |
| 7,956,131 B2 | 6/2011 | Arnold et al. |
| 7,994,356 B2 | 8/2011 | Awasthi et al. |
| 8,022,158 B2 | 9/2011 | Rathore et al. |
| 8,138,290 B2 | 3/2012 | Blackwell et al. |
| 8,163,206 B2 | 4/2012 | Chang et al. |
| 8,273,802 B2 | 9/2012 | Laredo et al. |
| 8,389,597 B2 | 3/2013 | Blackwell et al. |
| 8,399,538 B2 | 3/2013 | Steffen et al. |
| 8,415,404 B2 | 4/2013 | Nicolson et al. |
| 8,420,711 B2 | 4/2013 | Awasthi et al. |
| 8,450,387 B2 | 5/2013 | McCabe et al. |
| 8,470,906 B2 | 6/2013 | Rathore et al. |
| 8,487,058 B2 | 7/2013 | Liu et al. |
| 8,507,577 B2 | 8/2013 | Zanini et al. |
| 8,568,626 B2 | 10/2013 | Nicolson et al. |
| 8,637,621 B2 | 1/2014 | Iwata et al. |
| 8,703,891 B2 | 4/2014 | Broad |
| 8,937,110 B2 | 1/2015 | Alli et al. |
| 8,937,111 B2 | 1/2015 | Alli et al. |
| 8,940,812 B2 | 1/2015 | Reboul et al. |
| 8,980,972 B2 | 3/2015 | Driver |
| 9,006,279 B1 | 4/2015 | Tabuteau |
| 9,056,878 B2 | 6/2015 | Fujisawa et al. |
| 9,057,821 B2 | 6/2015 | Broad et al. |
| 9,079,927 B1 | 7/2015 | Tabuteau et al. |
| 9,125,808 B2 | 9/2015 | Alli et al. |
| 9,140,825 B2 | 9/2015 | Alli et al. |
| 9,156,934 B2 | 10/2015 | Alli et al. |
| 9,170,349 B2 | 10/2015 | Mahadevan et al. |
| 9,217,813 B2 | 12/2015 | Liu et al. |
| 9,244,196 B2 | 1/2016 | Scales et al. |
| 9,244,197 B2 | 1/2016 | Alli et al. |
| 9,260,544 B2 | 2/2016 | Rathore et al. |
| 9,297,928 B2 | 3/2016 | Molock et al. |
| 9,297,929 B2 | 3/2016 | Scales et al. |
| 10,618,257 B2 | 4/2020 | Suzuki et al. |
| 2010/0048847 A1 | 2/2010 | Broad |
| 2018/0037690 A1 | 2/2018 | Aitken et al. |
| 2018/0356558 A1 | 12/2018 | Ochrombel |
| 2019/0271798 A1 | 9/2019 | Mahadevan et al. |

FOREIGN PATENT DOCUMENTS

| | | |
|---|---|---|
| JP | 5560637 B2 * | 7/2014 |
| WO | 9207885 A1 | 5/1992 |
| WO | 1999029750 A1 | 6/1999 |
| WO | 2003022321 A2 | 3/2003 |
| WO | 2008061992 A2 | 5/2008 |
| WO | 2018009311 A1 | 1/2018 |
| WO | 2018026822 A1 | 2/2018 |
| WO | 2018067284 A1 | 4/2018 |
| WO | 2018230514 A1 | 12/2018 |

OTHER PUBLICATIONS

Dvorsky Drahomir, Database, CAPLUS, Mar. 15, 1988, pp. 1-1, Database accession No. 1989:596684.

Haddad Mohamed, Database, CAPLUS, Jan. 1, 2019, pp. 1-1, Database accession No. 2020:910681.

Matsumura Kiyotoshi., Database, CAPLUS, Mar. 18, 1987, pp. 1-8, Database accession No. 1987: 213645.

McKenna Charles., Database, CAPLUS, Mar. 30, 2017, pp. 1-1, Database accession No. 2017:522182.

PCT International Search Report, dated Aug. 18, 2021, for PCT Int'l Appln. No. PCT/IB2021/054496.

Rabbani Naila, Database, CAPLUS, Aug. 15, 2019, pp. 1-1, Database accession No. 2019:1566202.

Shikoku Chemicals., Database, CAPLUS, Dec. 6, 1984, pp. 1-1, Database accession No. 1985:185110.

Tabuteau Herriot., Database, CAPLUS, Sep. 16, 2014, pp. 1-1, Database accession No. 2014:1538193.

Troeger-Mueller Steffen., Database, CAPLUS, Jan. 1, 2017, pp. 1-1, Database accession No. 2017:963260.

* cited by examiner

IMIDAZOLIUM ZWITTERION POLYMERIZABLE COMPOUNDS AND OPHTHALMIC DEVICES INCORPORATING THEM

RELATED APPLICATIONS

This application claims priority to U.S. Provisional Patent Application Ser. No. 63/039,485, filed Jun. 16, 2020, which is incorporated herein by reference in its entirety.

FIELD OF THE INVENTION

The invention relates to imidazolium zwitterion polymerizable compounds, polymers made therefrom, and their use in ophthalmic devices and/or packaging solutions for ophthalmic devices.

BACKGROUND OF THE INVENTION

Contact lenses have been used commercially to improve vision since the 1950s. The first contact lenses were made of hard materials. Although these lenses are still currently used, they are not suitable for all patients due to their poor initial comfort and their relatively low permeability to oxygen. Later developments in the field gave rise to soft contact lenses, based upon hydrogels, which are extremely popular today. Many users find soft lenses are more comfortable, and increased comfort levels can allow soft contact lens users to wear their lenses longer than users of hard contact lenses.

Many users rely on contact lenses for their vision care needs and there is therefore a continuing drive in the industry to further improve the properties of contact lenses, and other ophthalmic devices, for instance to increase hydrophilicity or equilibrium water content, and/or to provide non-fouling or anti-microbial activity.

SUMMARY OF THE INVENTION

The invention relates to new zwitterion polymerizable compounds that are suitable for use in ophthalmic devices, such as contact lenses. The compounds may, for instance, be incorporated into the covalent structure of an ophthalmic device, or they be polymerized and used as coatings or non-covalently linked additives to the ophthalmic device. Polymers derives from the zwitterion polymerizable compounds may also be used as additives in packaging solutions for ophthalmic devices. Resultant ophthalmic devices exhibit favorable properties, including increased water content, which is particularly desirable in hydrogel contact lenses.

Accordingly, in one aspect, the invention provides a zwitterion polymerizable compound of formula I:

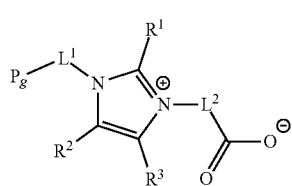

(I)

wherein $R^1$, $R^2$, and $R^3$ are independently H, alkyl, cycloalkyl, phenyl or benzyl;
$L^1$ and $L^2$ are each independently a linking group; and
$P_g$ is a polymerizable group.

In another aspect, the invention provides an ophthalmic device comprising a polymer derived from a zwitterion polymerizable compound as described herein.

In a further aspect, the invention provides a blister package including an ophthalmic device and a packaging solution, wherein the packaging solution comprises a polymer derived from a polymerizable zwitterion compound as described herein.

DETAILED DESCRIPTION OF THE INVENTION

It is to be understood that the invention is not limited to the details of construction or process steps set forth in the following description. The invention is capable of other embodiments and of being practiced or being carried out in various ways using the teaching herein.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula $[***]_n$, is used to depict the number of repeating units in a polymer's chemical formula, the formula should be interpreted to represent the number average molecular weight of the macromolecule.

The term "individual" includes humans and vertebrates.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The ophthalmic devices of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be optionally substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495, 313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Conventional hydrogels may also be formed from polyvinyl alcohol. Conventional hydrogel lenses may contain a coating, and the coating may be the same or different material from the substrate. Conventional hydrogels may include additives such as polyvinyl pyrrolidone, and comonomers including polymerizable derivatives of phosphoryl choline, methacrylic acid and the like. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of suitable families of hydrophilic components that may be present in the reactive mixture include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof. Silicone-containing components are well known and have been extensively described in the patent literature. For instance, the silicone-containing component may comprise at least one polymerizable group (e.g., a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing), at least one siloxane group, and one or more linking groups (which may be a bond) connecting the polymerizable group(s) to the siloxane group(s). The silicone-containing components may, for instance, contain from 1 to 220 siloxane repeat units. The silicone-containing component may also contain at least one fluorine atom. Silicone hydrogel lenses may contain a coating, and the coating may be the same or different material from the substrate.

Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244, 981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

The terms "reactive mixture" and "reactive monomer mixture" refer to the mixture of components (both reactive and non-reactive) which are mixed together and, when subjected to polymerization conditions, form the polymeric networks of the present invention as well as ophthalmic devices and contact lenses made therefrom. The reactive monomer mixture may comprise reactive components such as monomers, macromers, prepolymers, cross-linkers, and initiators, additives such as wetting agents, polymers, dyes, light absorbing compounds such as UV absorbers, pigments, dyes and photochromic compounds, any of which may be reactive or non-reactive but are capable of being retained within the resulting contact lens, as well as pharmaceutical and nutraceutical compounds, and any diluents. It will be appreciated that a wide range of additives may be added based upon the ophthalmic device which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a hydrogel contact lens that is made from at least one silicone-containing compound. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" refers to an optionally substituted linear or branched alkyl group containing the indicated number of carbon atoms. If no number is indicated, then alkyl (including any optional substituents on alkyl) may contain 1 to 16 carbon atoms. Preferably, the alkyl group contains 1 to 10 carbon atoms, alternatively 1 to 8 carbon atoms, alternatively 1 to 6 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, alkoxyalkyl, oxo ((=O)), carboxy, alkyl carboxy, carbonyl, alkoxy, thioalkyl, carbamate, carbonate, halogen, phenyl, benzyl, and combinations thereof. Preferred substituents include hydroxy, alkoxy, halo, alkoxyalkyl, or oxo groups. "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —$CF_3$— or —$CF_2CF_3$—. "Haloalkylene" means a divalent haloalkyl group, such as —$CH_2CF_2$—.

"Cycloalkyl" refers to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, alkoxyalkyl, carbonyl, alkoxy, thioalkyl, amido, carbamate, carbonate, halo, phenyl, benzyl, and combinations thereof. Preferred substituents include hydroxy, alkoxy, halo, alkoxyalkyl, or oxo groups. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, alkoxyalkyl, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —$CH_2CH_2NH$—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R_3Si$— and "siloxy" refers to a structure of formula $R_3Si$—O—, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[$CH_2CH_2O$]$_p$— or $CH_3O$—[$CH_2CH_2O$]$_p$—). Examples of alkyleneoxy include polyethyleneoxy, polypropyleneoxy, polybutyleneoxy, and poly(ethyleneoxy-co-propyleneoxy).

"Oxaalkylene" refers to an alkylene group as defined above where one or more non-adjacent $CH_2$ groups have been substituted with an oxygen atom, such as —$CH_2CH_2OCH(CH_3)CH_2$—. "Thiaalkylene" refers to an alkylene group as defined above where one or more non-adjacent CH₂ groups have been substituted with a sulfur atom, such as —CH₂CH₂SCH(CH₃)CH₂—.

The term "linking group" refers to a moiety that links a polymerizable group to the parent molecule. The linking group may be any moiety that is compatible with the compound of which it is a part, and that does not undesirably interfere with the polymerization of the compound, and is stable under the polymerization conditions as well as the conditions for the processing and storage of the final product. For instance, the linking group may be a bond, or it may comprise one or more alkylene, haloalkylene, amide, amine, alkyleneamine, carbamate, ester (—CO₂—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF₂—, —OCF₂CF₂—, —OCF₂CH₂—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups also include $C_1$-$C_8$ alkylene (preferably $C_2$-$C_6$ alkylene, such as ethylene or propylene), $C_1$-$C_8$ oxaalkylene (preferably $C_2$-$C_6$ oxaalkylene), $C_1$-$C_8$ alkylene-amide-$C_1$-$C_8$ alkylene, and $C_1$-$C_8$ alkylene-amine-$C_1$-$C_8$ alkylene, each of which is optionally substituted with 1 or 2 groups independently selected from hydroxyl and siloxy. Preferred linking groups further include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties (e.g., alkylene-cycloalkylene), the moieties may be present in any order. Notwithstanding this, the listing order represents the preferred order in which the moieties appear in the compound starting from the terminal polymerizable group to which the linking group is attached.

"Optionally substituted" means that a moiety may contain one or more optional substituents. The term "optional substituent" means that a hydrogen atom in the underlying moiety is optionally replaced by a substituent. Any substituent may be used that is sterically practical at the substitution site and is synthetically feasible. Identification of suitable optional substituents is well within the capabilities of an ordinarily skilled artisan. Examples of an "optional substituent" include, without limitation, $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^4R^5$, benzyl, $SO_3H$, $SO_3Na$, or —Y—$P_g$, wherein $R^4$ and $R^5$ are independently H or $C_1$-$C_6$ alkyl, Y is a linking group; and $P_g$ is a polymerizable group. The foregoing substituents may be optionally substituted by an optional substituent (which, unless otherwise indicated, is preferably not further substituted). For instance, alkyl may be substituted by halo (resulting, for instance, in $CF_3$).

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

As noted above, the invention provides zwitterion polymerizable compounds. The compounds are of formula I:

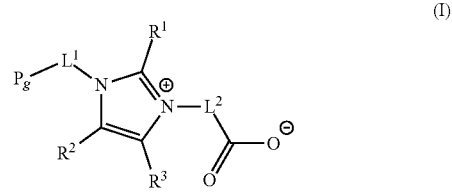

(I)

wherein $R^1$, $R^2$, and $R^3$ are independently H, alkyl, cycloalkyl, phenyl or benzyl;
$L^1$ and $L^2$ are each independently a linking group; and
$P_g$ is a polymerizable group.
$R^1$ in the compound of formula I may be H. $R^1$ in the compounds of formula I maybe or $C_1$-$C_6$ alkyl, preferably $C_1$-$C_3$ alkyl, more preferably methyl.
$R^2$ in the compound of formula I may be H.
$R^3$ in the compound of formula I may be H.
$L^1$ and $L^2$ in the compound of formula I may be independently alkylene, cycloalkylene, heterocycloalkylene, arylene, heteroarylene, oxaalkylene, alkylene-amide-alkylene, alkylene-amine-alkylene, or combinations thereof.
$L^1$ and $L^2$ may be independently alkylene, preferably independently $C_2$-$C_6$ alkylene. Each alkylene is optionally substituted, for instance with 1 or 2 groups independently selected from hydroxy, alkoxy, halo, alkoxyalkyl, and oxo.
$P_g$ in the compound of formula I may be styryl, vinyl carbonate, vinyl ether, vinyl carbamate, N-vinyl lactam, N-vinylamide, (meth)acrylate, or (meth)acrylamide.
$P_g$ may be (meth)acrylate or (meth)acrylamide.
$P_g$ may be methacrylate.
Exemplary compounds of formula I are shown in Table 1.

TABLE 1

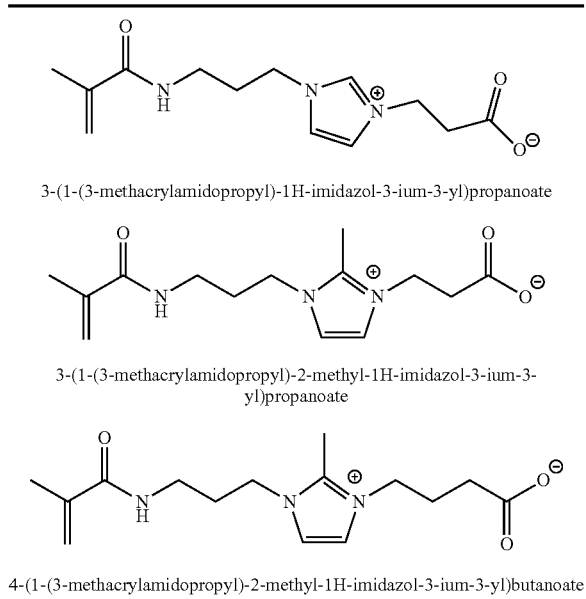

3-(1-(3-methacrylamidopropyl)-1H-imidazol-3-ium-3-yl)propanoate 3-(1-(3-methacrylamidopropyl)-2-methyl-1H-imidazol-3-ium-3-yl)propanoate 4-(1-(3-methacrylamidopropyl)-2-methyl-1H-imidazol-3-ium-3-yl)butanoate The zwitterion polymerizable compounds of the invention may be formed into polymers for incorporation in ophthalmic devices by a variety of techniques. For example, the compounds may be homo- or co-polymerized into polymers that are then coated onto an ophthalmic device or added to the reactive monomer mixture from which the ophthalmic device is made (to, for instance, form a semi interpenetrating network with the other components of the reactive monomer mixture).

A zwitterion polymerizable compound according to the invention may also be incorporated in an ophthalmic device via grafting, as further demonstrated by the Examples. Exemplary grafting techniques are described in U.S. pre-grant publication 20180037690, which is incorporated herein by reference in its entirety.

In addition, a zwitterion polymerizable compound according to the invention may added to a reactive monomer mixture containing other monomers suitable for making the ophthalmic device and reacted therewith under free radical polymerization conditions to form polymers from which the ophthalmic device may be made. Such reactive mixtures may comprise, in addition to a zwitterion polymerizable compound as described above, one or more monomers suitable for making the desired ophthalmic device, as well as optional ingredients. Thus, the reactive mixture may, for instance, contain: hydrophilic components, hydrophobic components, silicone-containing components, wetting agents such as polyamides, crosslinking agents, and further components such as diluents and initiators.

Hydrophilic Components

Examples of suitable families of hydrophilic monomers include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth)acrylamide, N-(3-hydroxybutyl) (meth)acrylamide, N-(4-hydroxybutyl) (meth)acrylamide, 2-aminoethyl (meth)acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth)acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-β-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl)amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl)dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof.

Non-limiting examples of hydrophilic O-vinyl carbamates and O-vinyl carbonates monomers include N-2-hydroxyethyl vinyl carbamate and N-carboxy-ß-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer that may be present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, or mixtures of the foregoing; one or more optionally repeating siloxane units; and one or more linking groups connecting the polymerizable groups to the siloxane units.

Formula A. The silicone-containing component may comprise one or more polymerizable compounds of Formula A:

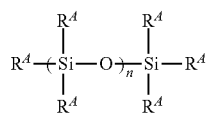

Formula A wherein:

at least one $R^A$ is a group of formula $R_g$-L- wherein $R_g$ is a polymerizable group and L is a linking group, and the remaining $R^A$ are each independently:

(a) $R_g$-L-, (b) $C_1$-$C_{16}$ alkyl optionally substituted with one or more hydroxy, amino, amido, alkoxyalkyl, carboxy, alkyl carboxy, carbonyl, alkoxy, amido, carbamate, carbonate, halo, phenyl, benzyl, or combinations thereof, (c) $C_3$-$C_{12}$ cycloalkyl optionally substituted with one or more alkyl, hydroxy, amino, amido, alkoxyalkyl, carbonyl, alkoxy, amido, carbamate, carbonate, halo, phenyl, benzyl, or combinations thereof, (d) a $C_6$-$C_{14}$ aryl group optionally substituted with one or more alkyl, hydroxy, amino, amido, alkoxyalkyl, carboxy, alkyl carboxy, carbonyl, alkoxy, amido, carbamate, carbonate, halo, phenyl, benzyl, or combinations thereof, (e) halo, (f) alkoxy, cyclic alkoxy, or aryloxy, (g) siloxy, (h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or (i) a monovalent siloxane chain comprising from 1 to 100 siloxane repeat units optionally substituted with alkyl, alkoxy, hydroxy, amino, alkoxyalkyl, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Examples of silicone-containing components suitable for use in the invention include, but are not limited to, compounds listed in Table A. Where the compounds in Table A contain polysiloxane groups, the number of SiO repeat units in such compounds, unless otherwise indicated, is preferably from 3 to 100, more preferably from 3 to 40, or still more preferably from 3 to 20.

TABLE A 1 mono-methacryloxypropyl terminated mono-n-butyl terminated polydimethylsiloxanes (mPDMS) (preferably containing from 3 to 15 SiO repeating units)
2 mono-acryloxypropyl terminated mono-n-butyl terminated polydimethylsiloxane
3 mono(meth)acryloxypropyl terminated mono-n-methyl terminated polydimethylsiloxane
4 mono(meth)acryloxypropyl terminated mono-n-butyl terminated polydiethylsiloxane
5 mono(meth)acryloxypropyl terminated mono-n-methyl terminated polydiethylsiloxane
6 mono(meth)acrylamidoalkylpolydialkylsiloxanes
7 mono(meth)acryloxyalkyl terminated mono-alkyl polydiarylsiloxanes
8 3-methacryloxypropyltris(trimethylsiloxy)silane (TRIS)
9 3-methacryloxypropylbis(trimethylsiloxy)methylsilane
10 3-methacryloxypropylpentamethyl disiloxane
11 mono(meth)acrylamidoalkylpolydialkylsiloxanes
12 mono(meth)acrylamidoalkyl polydimethylsiloxanes TABLE A-continued 13 N-(2,3-dihydroxypropane)-N'-(propyl tetra(dimethylsiloxy) dimethylbutylsilane)acrylamide
14 N-[3-tris(trimethylsiloxy)silyl]-propyl acrylamide (TRIS-Am)
15 2-hydroxy-3-[3-methyl-3,3-di(trimethylsiloxy)silylpropoxy]-propyl methacrylate (SiMAA)
16 2-hydroxy-3-methacryloxypropyloxypropyl-tris(trimethylsiloxy)silane 17 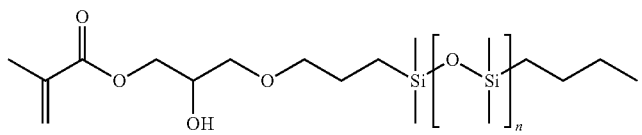
mono-(2-hydroxy-3-methacryloxypropyloxy)-propyl terminated mono-n-butyl terminated polydimethylsiloxanes (OH-mPDMS) (containing from 4 to 30, or from 4 to 20, or from 4 to 15 SiO repeat units)

18 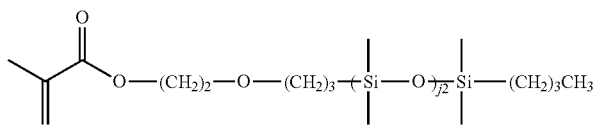

19 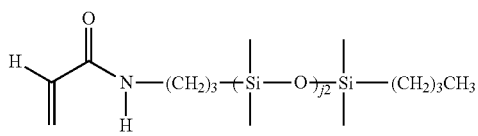

20 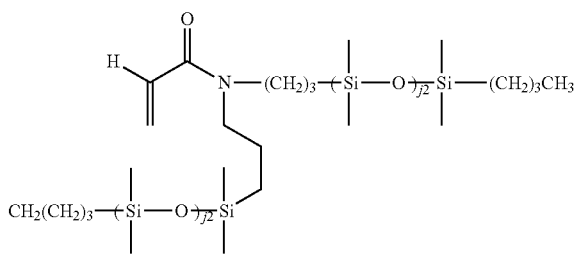

21 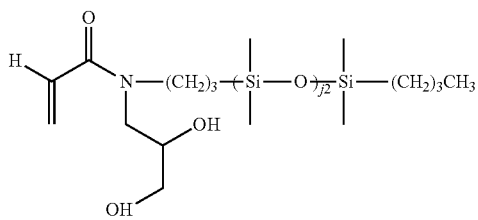

22 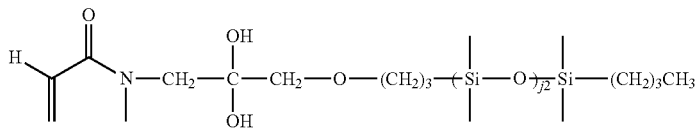

23 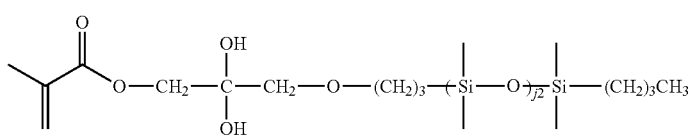

TABLE A-continued

24
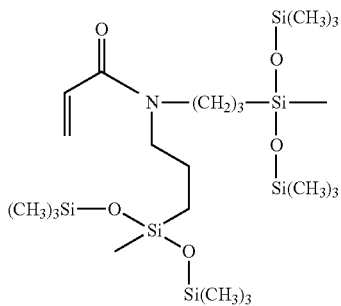

Additional non-limiting examples of suitable silicone-containing components are listed in Table B. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE B

25
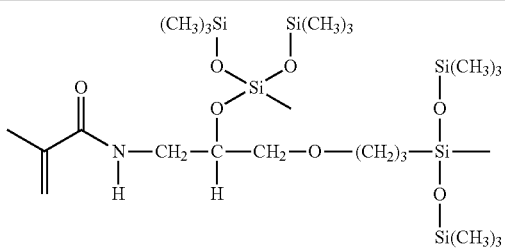

26
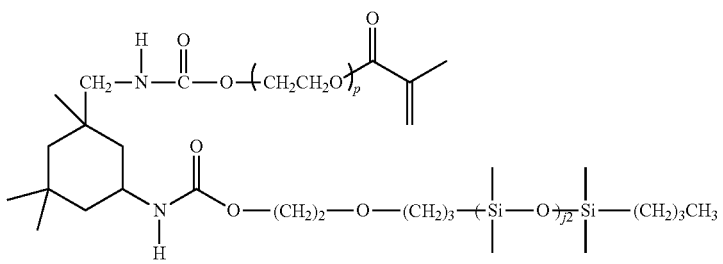

p is 1 to 10

27
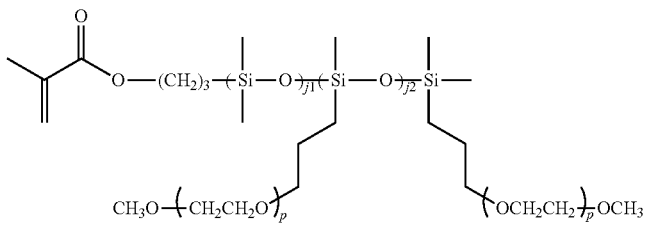

p is 5-10

28
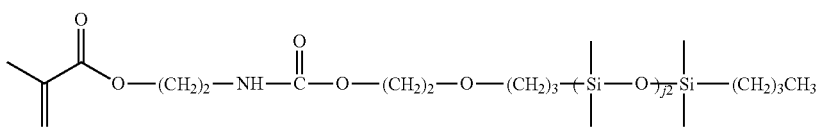

29
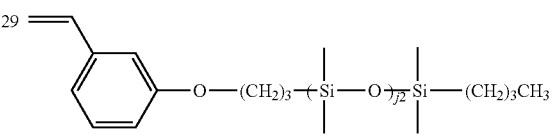

TABLE B-continued 30 1,3-bis[4-(vinyloxycarbonyloxy)but-1-yl]tetramethyl-disiloxane
31 3-(vinyloxycarbonylthio)propyl-[tris(trimethylsiloxy)silane]
32 3-[tris(trimethylsiloxy)silyl]propyl allyl carbamate
33 3-[tris(trimethylsiloxy)silyl]propyl vinyl carbamate
34 tris(trimethylsiloxy)silylstyrene (Styryl-TRIS)

35 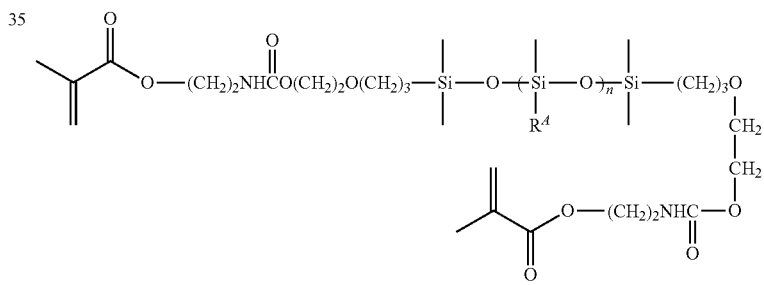

$R^A = CH_3$ (a) or $CH_2CH_2CF_3$ (b) or $CH_2$—$(CH_2)_2$—$[OCH_2CH_2]_{1-10}$—$OCH_3$ (c);
$a + b + c = n$

36 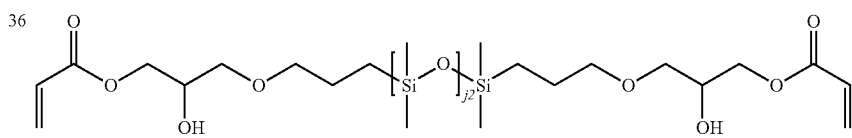

37 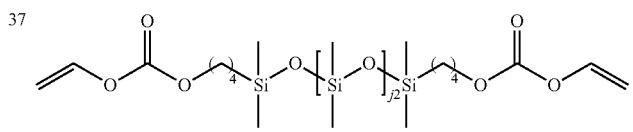

38 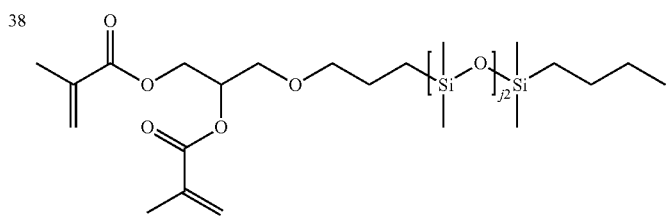

39 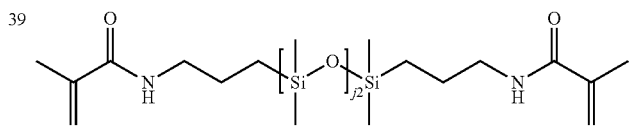

40 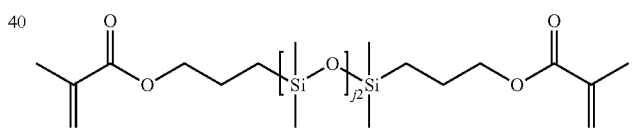

41 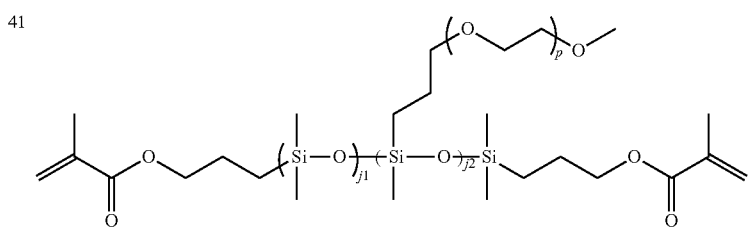

$j1 = 80\text{-}90$
$j2 = 5\text{-}6$
$p = 7\text{-}8$

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G and G1:

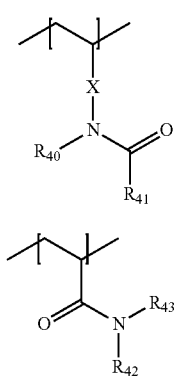

Formula G

Formula G1 wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted C$_1$ to C$_2$ alkyl groups. X may be a direct bond, and R$_{40}$ and R$_{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula G or Formula G1, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methyl-propionamide, N-vinyl-N, N'-dimethylurea, N, N-dimethylacrylamide, methacrylamide, and acyclic amides of Formulae G2 and G3:

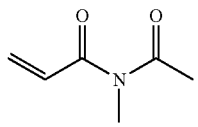

Formula G2

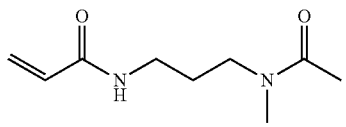

Formula G3

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

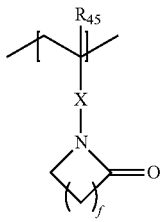

Formula G4 wherein R$_{45}$ is a hydrogen atom or methyl group; wherein f is a number from 1 to 10; wherein X is a direct bond, —(CO)—, or —(CONHR$_{46}$)—, wherein R$_{46}$ is a C$_1$ to C$_3$ alkyl group. In Formula G4, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula G4, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth) acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-O-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N, N-trimethyl-9-oxo-, inner salt, 4-oxide (9CI) (PBT, phosphobetaine, CAS 163674-35-9, 2-methacryloyloxyethyl phosphorylcholine, 3-(dimethyl(4-vinylbenzyl)ammonio) propane-1-sulfonate (DMVBAPS), 3-((3-acrylamidopropyl) dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethylacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a Mw of about 570 KDa).

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multifunctional macromers, and prepolymers, to the reactive mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes a, w-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described above, such as the multi-functional compounds shown in Table B.

Further Constituents

The reactive mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445, the disclosure of which is incorporated herein by reference.

Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms.

Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino)ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like.

If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine oxide (Irgacure 819), 2,4,6-trimethylbenzyldiphenyl phosphine oxide and 2,4,6-trimethylbenzoyl diphenylphosphine oxide, benzoin methyl ester and a combination of cam-phorquinone and ethyl 4-(N,N-dimethylamino)benzoate.

Commercially available (from IGM Resins B.V., The Netherlands) visible light initiator systems include Irgacure® 819, Irgacure® 1700, Irgacure® 1800, Irgacure® 819, Irgacure® 1850 and Lucrin® TPO initiator. Commercially available (from IGM Resins B.V.) UV photoinitiators include Darocur® 1173 and Darocur® 2959. These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the ophthalmic devices of the invention may comprise, in addition to a zwitterionic polymerizable compound of formula I, any of the other polymerizable compounds and optional components described above.

Preferred reactive mixtures may comprise: a zwitterionic polymerizable compound of formula I, and a hydrophilic component.

Preferred reactive mixtures may comprise: a zwitterionic polymerizable compound of formula I, and a hydrophilic component selected from DMA, NVP, HEMA, VMA, NVA, methacrylic acid, and mixtures thereof. Preferred are mixtures of HEMA and methacrylic acid.

Preferred reactive mixtures may comprise: a zwitterionic polymerizable compound of formula I, a hydrophilic component, and a silicone-containing component.

Preferred reactive mixtures may comprise: a zwitterionic polymerizable compound of formula I, a hydrophilic component, and a silicone-containing component comprising a compound of formula A.

Preferred reactive mixtures may comprise: a zwitterionic polymerizable compound of formula I, a hydrophilic component selected from DMA, NVP, HEMA, VMA, NVA, and mixtures thereof; a silicone-containing component such as a compound of formula A; and an internal wetting agent.

Preferred reactive mixtures may comprise: a zwitterionic polymerizable compound of formula I, a hydrophilic component selected from DMA, HEMA and mixtures thereof; a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof; and a wetting agent (preferably PVP or PVMA). For the hydrophilic component, mixtures of DMA and HEMA are preferred. For the silicone containing component, mixtures of SiMAA and mPDMS are preferred.

Preferred reactive mixtures may comprise: a zwitterionic polymerizable compound of formula I, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive mixture further comprises a silicone-containing crosslinker, such as ac-PDMS. Also preferably, the reactive mixture contains a wetting agent (preferably DMA, PVP, PVMA or mixtures thereof).

Preferred reactive mixtures may comprise: a zwitterionic polymerizable compound of formula I; between about 1 and about 15 wt % of at least one polyamide (e.g., an acyclic polyamide, a cyclic polyamide, or mixtures thereof); at least one first mono-functional, hydroxyl substituted poly(disubstituted siloxane) having 4 to 8 siloxane repeating units (e.g., OH-mPDMS where n is 4 to 8, preferably n is 4); at least one second hydroxyl substituted poly(disubstituted siloxane) that is a mono-functional hydroxyl substituted poly(disubstituted siloxane)s having 10 to 200 or 10-100 or 10-50 or 10-20 siloxane repeating units (e.g., OH-mPDMS where n is 10 to 200 or 10-100 or 10-50 or 10-20, preferably n is 15); about 5 to about 35 wt % of at least one hydrophilic monomer; and optionally a multifunctional hydroxyl substituted poly(disubstituted siloxane)s having 10 to 200, or 10 to 100 siloxane repeating units (e.g., ac-PDMS). Preferably, the first mono-functional, hydroxyl substituted poly(disubstituted siloxane) and the second hydroxyl substituted poly(disubstituted siloxane) are present in concentrations to provide a ratio of weight percent of the first mono-functional, hydroxyl substituted poly(disubstituted siloxane) to weight percent of the second hydroxyl substituted poly(disubstituted siloxane) of 0.4-1.3, or 0.4-1.0.

The foregoing reactive mixtures may contain optional ingredients such as, but not limited to, one or more initiators, internal wetting agents, crosslinkers, UV or high energy visible light absorbers, and diluents.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, ophthalmic devices may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a molded ophthalmic device, such as a silicone hydrogel contact lens, may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

Silicone hydrogel ophthalmic devices (e.g., contact lenses) according to the invention preferably exhibit the following properties. All values are prefaced by "about," and the devices may have any combination of the listed properties. The properties may be determined by methods known to those skilled in the art, for instance as described in United States pre-grant publication US20180037690, which is incorporated herein by reference.

Equilibrium water content %: at least 20%, or at least 25% and up to 80% or up to 70%

Haze: 30% or less, or 10% or less

Advancing dynamic contact angle (Wilhelmy plate method): 100° or less, or 80° or less; or 50° or less Tensile Modulus (psi): 150 or less, or 135 or less, 120 or less, or 80 to 135

Oxygen permeability (Dk, barrers): at least 60 barrers, or at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less.

In addition to being incorporated into an ophthalmic device by the methodologies described above, the zwitterionic polymerizable compounds may alternatively (or in addition) be used in blister package packaging solutions. Thus, according to this embodiment, a blister package may be provided that includes an ophthalmic device and a packaging solution, wherein the packaging solution comprises a polymer derived from a polymerizable zwitterion compound as described above.

Blister packages generally comprise a bowl portion and a foil top. These packages house the soft contact lens and its aqueous packaging solution. The bowl portion may be made from any suitable material. Typically, the bowl portion is made from a hydrophobic material such as polypropylene. Polypropylene is a commonly used material for contact lens packages. Polypropylene is resilient enough to withstand the sterilization steps of contact lens manufacture, and can be injection molded into a number suitable shapes and sizes. See, U.S. Pat. Nos. 4,691,820; 5,054,610; 5,337,888; 5,375,698; 5,409,104; 5,467,868; 5,515,964; 5,609,246; 5,695,049; 5,697,495; 5,704,468; 5,711,416; 5,722,536; 5,573,108; 5,823,327; 5,704,468; 5,983,608; 6,029,808; 6,044,966; and 6,401,915 for non-limiting examples of such packaging, all of which are hereby incorporated by reference in their entirety.

Packaging solutions for use with ophthalmic devices, such as contact lenses, are well known. Suitable solutions include, without limitation, saline solutions, other buffered solutions, and deionized water. For instance the packaging solution may be a saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution.

Some embodiments of the invention will now be described in detail in the following Examples.

EXAMPLES

The test methods used to characterize contact lenses are described below. Some abbreviations were used in the tables as headings, and some standard deviations were reported in the tables inside parentheses.

Water content was measured gravimetrically. Lenses were equilibrated in packing solution for 24 hours. Each of three test lenses is removed from packing solution using a sponge tipped swab and placed on blotting wipes which have been dampened with packing solution. Both sides of the lens are contacted with the wipe. Using tweezers, the test lens is placed in a tared weighing pan and weighed. Then two more sets of samples are prepared and weighed. All weight measurements were done in triplicate, and the average of those values used in the calculations. The wet weight is defined as the combined weight of the pan and wet lenses minus the weight of the weighing pan alone.

The dry weight was measured by placing the sample pans in a vacuum oven which has been preheated to 60° C. for 30 minutes. Vacuum was applied until the pressure reaches at least 1 inch of Hg is attained; lower pressures are allowed. The vacuum valve and pump are turned off and the lenses are dried for at least 12 hours, typically overnight. The purge valve is opened allowing dry air or dry nitrogen gas to enter. The oven is allowed to reach atmospheric pressure. The pans are removed and weighed. The dry weight is defined as the combined weight of the pan and dry lenses minus the weight of the weighing pan alone. The water content of the test lens was calculated as follows: % water content (% WC)=(wet weight−dry weight)/wet weight×100. The average water content and its standard deviation were calculated, and the average value reported as the percent water content of the test lens. Standard deviations are listed in the table in the parentheses.

The percent grafted weight gain (% GWG) was calculated as follows: (dry weight of the grafted lens−dry weight of the substrate lens)/dry weight of the substrate lens×100. Both the grafted lens and the substrate lens were equilibrated in deionized water for several hours to remove any residual salts prior to vacuum drying. Typically, at least three lenses are weighed and averaged for each sample.

The refractive index (RI) of a contact lens was measured by a Leica ARIAS 500 Abbe refractometer in manual mode or by a Reichert ARIAS 500 Abbe refractometer in automatic mode with a prism gap distance of 100 microns. The instrument was calibrated using deionized water at 20° C. (+/−0.2° C.). The prism assembly was opened, and the test lens placed on the lower prism between the magnetic dots closest to the light source. If the prism is dry, a few drops of saline were applied to the bottom prism. The front curve of the lens was against the bottom prism. The prism assembly was then closed. After adjusting the controls so that the shadow line appeared in the reticle field, the refractive index was measured. The RI measurement was made on five test lenses. The average RI calculated from the five measurements was recorded as the refractive index as well as its standard deviation.

The invention is now described with reference to the following examples. Before describing several exemplary embodiments of the invention, it is to be understood that the invention is not limited to the details of construction or process steps set forth in the following description. The invention is capable of other embodiments and of being practiced or being carried out in various ways.

The following abbreviations will be used throughout the Examples and have the following meanings:

DMA: N, N-dimethylacrylamide (Jarchem)
HEMA: 2-hydroxyethyl methacrylate (Bimax)
CBT: 1-Propanaminium, N-(2-carboxyethyl)-N,N-dimethyl-3-[(1-oxo-2-propen-1-yl)amino]-, inner salt; carboxybetaine; CAS 79704-35-1

Norbloc: 2-(2-hydroxy-5-methacrylyloxyethylphenyl)-2H-benzotriazole (Janssen)
Blue HEMA: 1-amino-4-[3-(4-(2-methacryloyloxy-ethoxy)-6-chlorotriazin-2-ylamino)-4-sulfophenylamino]anthraquinone-2-sulfonic acid, as described in U.S. Pat. No. 5,944,853
PVP K90: poly(N-vinylpyrrolidone) (ISP Ashland)
EGDMA: ethylene glycol dimethacrylate (Esstech)
TEGDMA: tetraethylene glycol dimethacrylate (Esstech)
AIBN: azobisisobutyronitrile
Omnirad 403: bis(2,6-dimethoxybenzoyl)-2,4,4-trimethylpentylphosphine oxide
Omnirad 819: bis(2,4,6-trimethylbenzoyl)-phenylphosphineoxide (IGM Resins)
Omnirad 1173: 2-hydroxy-2-methyl-1-phenylpropanone
Omnirad: 1700: mixture of 25 weight % Omnirad 403 and 75 weight % Omnirad 1173
TEMPO: (2,2,6,6-tetramethylpiperidin-1-yl)oxyl or (2,2,6,6-tetramethylpiperidin-1-yl)oxidanyl
HO-mPDMS: mono-n-butyl terminated mono-(2-hydroxy-3-methacryloxypropyl)-propyl ether terminated polydimethylsiloxane ($M_n$=400-1500 g/mol) (Ortec or DSM-Polymer Technology Group)

HO-mPDMS (n=4):

HO-mPDMS (n=15):

nBu: n-butyl
PP: polypropylene which is the homopolymer of propylene
Z: Zeonor which is a polycycloolefin thermoplastic polymer (Nippon Zeon Co Ltd)
D3O: 3,7-dimethyl-3-octanol (Vigon)
BAGE: Boric Acid Glycerol Ester (molar ratio of boric acid to glycerol was 1:2) 299.3 grams (mol) of glycerol and 99.8 grams (mol) of boric acid were dissolved in 1247.4 grams of a 5% (w/w) aqueous ethylenediaminetetraacetic acid solution in a suitable reactor and then heated with stirring to 90-94° C. under mild vacuum (2-6 torr) for 4-5 hours and allowed to cool down to room temperature.
Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask.
mL: milliliter(s)
nm: nanometer(s)
LED: light emitting diode(s)
TL03 lights: Phillips TLK 40 W/03 bulbs
NMR: nuclear magnetic resonance spectroscopy
$D_2O$: deuterium oxide Example 1

Synthesis of 3-(1-(3-methacrylamidopropyl)-1H-imidazol-3-ium-3-yl)propanoate (A)

-continued

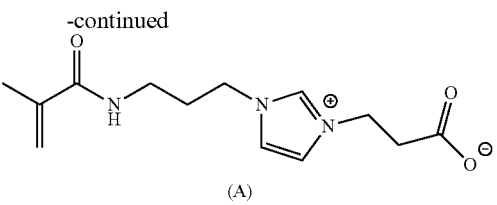

(A)

A solution of 1-(3-methacrylamidopropyl)-1H-imidazole (19.3 grams, 0.1 moles) and ethyl-3-bromopropionate (19.0 grams, 0.105 moles) in 10 mL of ethanol was heated at 80° C. with constant stirring. After eight hours, the mixture was cooled to room temperature, and the ethyl alcohol was evaporated under reduced pressure. The residual material was dissolved in 150 mL of water and washed three times with 100 mL of ethyl acetate. After the addition of 0.1 grams of butylated hydroxytoluene, the volatile organic components were evaporated at a pressure of 50 mm Hg while maintaining the temperature ≤20° C. Sodium carbonate (15 g, ~1.4 eq.) was added to the aqueous solution and stirred for 24 hours at room temperature. After rotary evaporation of water, the residual solids are washed with warm acetonitrile (2×150 mL) and the liquids decanted. The rude product is redissolved in a (5:95) ethyl alcohol:acetonitrile mixture and filtered. After the addition of 150 mg of butylated hysroxytoluene to the filtrate, the solvents are evaporated under reduced pressure and the resulting solids are washed with ethyl acetate and further dried in a rotary evaporator to yield the desired product (compound (A)). Compound (A) is 3-(1-(3-methacrylamidopropyl)-1H-imidazol-3-ium-3-yl) propanoate. $^1$H NMR (500 MHz, $D_2O$) δ (ppm): 1.93 (3H, s, $CH_3$), 2.18 (2H, dddd, J=6.5 Hz, $CH_2$), 2.77 (2H, t, J=7 Hz, $CH_2$), 3.35 (2H, t, J=6.5 Hz, $CH_2$), 4.28 (2H, t, J=7 Hz, $CH_2$), 4.43 (2H, t, J=6.5 Hz), 5.48 (1H, bs, vinylic), 5.70 (1H, bs, vinylic), 7.54-7.55 (2H, dd, J=5, 2 Hz, Ar—H), 8.83 (1H, bs, Ar—H).

Example 2

Synthesis of 3-(1-(3-methacrylamidopropyl)-2-methyl-1H-imidazol-3-ium-3-yl)propanoate (B)

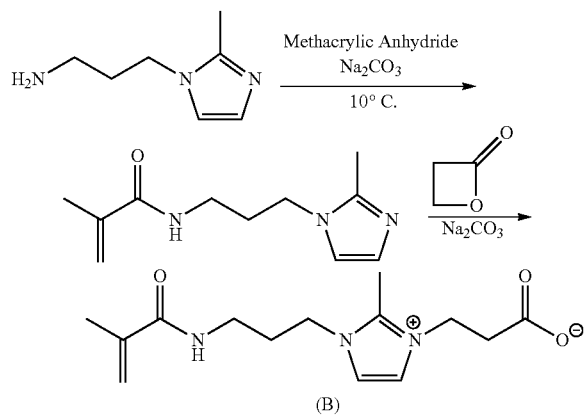

(B)

Methacrylic anhydride (34 grams, 0.22 moles) was added in a dropwise fashion to a chilled and stirred suspension of 2-methyl-1-(3-aminopropyl)-1H-imidazole (27.8 grams, 0.2 moles) and 23.32 grams of sodium carbonate (0.22 moles) in water, while maintaining the temperature below 10° C. The solution warmed up to room temperature and stirred for an additional hour. After adding 0.05 grams of butylated hydroxytoluene to the reaction mixture, the volatile components were evaporated under reduced pressure with the temperature below 20° C. The product was re-dissolved in a 75:25 (v/v) mixture of ethyl acetate and hexanes and filtered through a short silica gel plug. The solvents were then evaporated under reduced pressure, and the product was used "as is" for the subsequent alkylation reaction to form the desired zwitterion. 2-methyl-1-(3-acrylamidopropyl)-1H-imidazole (10.4 grams, 0.05 moles) and β-lactone (3.6 grams, 0.06 moles) were dissolved in 50 mL of ethyl alcohol containing 100 milligrams of suspended sodium carbonate. The mixture was stirred at room temperature for 20 hours, after which the solution appeared to contain a single major product by thin layer chromatography. 100 mL of ethyl acetate was added, and the mixture was vacuum filtered through a fritted glass funnel to remove the sodium carbonate. All volatile components were evaporated under reduced pressure, while maintaining the temperature below 20° C. The residue was washed at less twice with warm ethyl acetate and vacuum filtered over a fritted glass funnel. The filtrates were dried under reduced pressure to yield the desired product (compound (B)). $^1$H NMR (500 MHz, $D_2O$) δ (ppm): 1.93 (3H, s, $CH_3$), 2.11 (2H, m, $CH_2$), 2.64 (3H, s, $CH_3$), 2.65-2.69 (2H, m, $CH_2$), 3.35 (2H, t, J=6.75 Hz, $CH_2$), 4.17 (2H, m, $CH_2$), 4.33 (2H, m, $CH_2$), 5.48 (1H, s, vinylic), 5.70 (1H, s, vinylic), 7.42 (2H, s, vinylic).

Example 3

Synthesis of 4-(1-(3-methacrylamidopropyl)-2-methyl-1H-imidazol-3-ium-3-yl)butanoate (C)

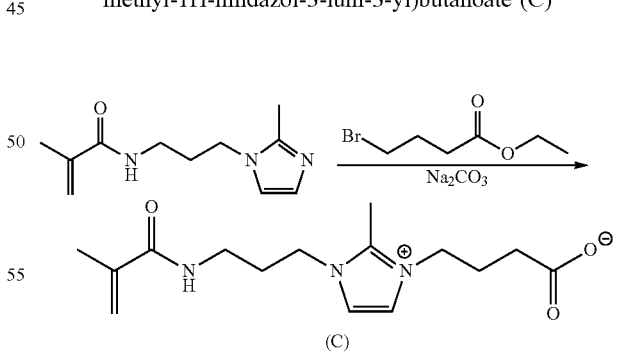

(C)

A solution of 2-methyl-1-(3-acrylamidopropyl)-1H-imidazole (10 grams, 0.048 moles) and 10.3 grams of ethyl 4-bromobutyrate (1.1 equivalents) in 20 mL of ethanol was heated at 80° C. while stirring and monitoring the reaction by thin layer chromatography. The mixture was cooled to room temperature after overnight stirring; 0.100 grams of BHT were added; and the volatile components were evaporated under reduced pressure while maintaining the temperature below 20° C. The product was dissolved in water, and the mixture was extracted three times with 100 mL of ethyl acetate to remove the unreacted ethyl 4-bromobutyrate. 0.100 Grams of butylated hydroxytoluene and 6.0 grams of sodium carbonate (0.056 moles) were added to the aqueous portion. The aqueous portion was then stirred at room temperature to generate the desired zwitterion. Once the reaction was complete, the volatile components were evaporated under reduced pressure with the temperature maintained below 20° C. The product was re-dissolved in 10% (v/v) ethyl alcohol in acetonitrile, and the resulting suspension was filtered to remove the residual sodium carbonate. The volatile solvents were removed from the filtrate under reduced pressure maintaining a temperature below 20° C. The product (compound (C)) was washed with warm acetonitrile over a fritted glass funnel to obtain the desired zwitterion. $^1$H NMR (500 MHz, $D_2O$) δ (ppm): 1.94 (3H, s, $CH_3$), 2.07 (1H, m, $CH_2$), 2.14 (1H, m, $CH_2$), 2.24 (2H, t, J=7.5 Hz, $CH_2$), 2.63 (3H, s, $CH_3$), 3.37 (2H, t, J=7.25 Hz, $CH_2$), 4.15 (2H, t, J=7.25 Hz, $CH_2$), 4.20 (2H, t, J=7.25 Hz), $CH_2$), 5.48 (1H, s, vinylic), 5.70 (1H, s, vinylic), 7.44 (2H, s, Ar—H).

Example 4—Grafted Silicone Hydrogel Contact Lenses

A reactive monomer mixture was prepared composed of 75 weight percent of the formulation listed in Table 2 and 25 weight percent of the diluent D3O. The reactive monomer mixture was filtered through a 3 μm filter using a stainless-steel syringe under pressure and subsequently degassed under reduce pressure for about thirty minutes. In a glove box with a nitrogen gas atmosphere and less than 0.2 percent oxygen gas (v/v), about 75-100 μL of the reactive mixture were dosed using an Eppendorf pipet at room temperature into the front curve mold made of Zeonor. The base curve mold made of a 55:45 (w/w) blend of Zeonor and polypropylene was then placed onto the front curve mold. The molds were equilibrated for a minimum of twelve hours in the glove box prior to dosing. A plate containing about four pallets, each pallet containing eight lens mold assemblies, was transferred into an adjacent glove box maintained at about 62° C., and the lenses were cured from the top for 12 minutes using 435 nm LED lights having intensity of 4 mW/cm$^2$.

Working under yellow lights and limiting general exposure to additional light exposure (e.g., by wrapping containers with aluminum foil, etc.), the lenses were manually de-molded with most lenses adhering to the front curve mold and released by suspending the lenses in 70 percent isopropanol for about one or two hours (about one lens per 15 mL), sometimes overnight, followed by washing two times with 70 percent isopropanol, two times with deionized water, and finally stored in deionized water in the refrigerator in aluminum foil covered containers. These lenses (4A) comprised covalently bound monoacylphosphine oxide groups from which chemical grafting reactions may be initiated. Each washing step lasted about 30 minutes. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all lenses without defects and transition from diluent swollen networks to the deionized water or packaging solution swollen hydrogels.

25 Lenses (4A) were suspended in 50 mL of a 10% (w/v) CBT solution of 50:50 (v/v) aqueous 1, 2-propylene glycol in a 100 mL glass jar and degassed for 15 minutes under reduced pressure (ca. 40 mm Hg) and purged with nitrogen gas aeration. The jar was capped and transferred into glove box with a nitrogen gas atmosphere with less than 0.2 percent oxygen gas (v/v) and a temperature of 55° C. and equilibrated on a shaker (180 rpm) for 90 minutes. The temperature of the suspension was then 55° C. The cap was replaced by a clear plastic cover, and the suspension was irradiated using 420 LEDs from the top having an intensity of 1.2 mW/cm$^2$ for 20 minutes while still being shaken. After irradiation, the lenses were removed and washed two times with deionized water and two times with borate buffered packing solution. The lenses were stored in vials. After one day of equilibration, the lenses were inspected and sterilized by autoclaving at 122° C. for 30 minutes. The lenses (4B) were equilibrated 3-4 days after sterilization, and then, the physical properties of the sterile lenses were measured as listed in Table 3.

25 Lenses (4A) were suspended in 50 mL of a 10% (w/v) compound (B) solution of 50:50 (v/v) aqueous 1, 2-propylene glycol in a 100 mL glass jar and degassed for 15 minutes under reduced pressure (ca. 40 mm Hg) and purged with nitrogen gas aeration. The jar was capped and transferred into glove box with a nitrogen gas atmosphere with less than 0.2 percent oxygen gas (v/v) and a temperature of 55° C. and equilibrated on a shaker (180 rpm) for 90 minutes. The temperature of the suspension was then 55° C. The cap was replaced by a clear plastic cover, and the suspension was irradiated using 420 LEDs from the top having an intensity of 1.2 mW/cm$^2$ for 20 minutes while still being shaken. After irradiation, the lenses were removed and washed two times with deionized water and two times with borate buffered packing solution. The lenses were stored in vials. After one day of equilibration, the lenses were inspected and sterilized by autoclaving at 122° C. for 30 minutes. The lenses (4C) were equilibrated 3-4 days after sterilization, and then, the physical properties of the sterile lenses were measured as listed in Table 3.

25 Lenses (4A) were suspended in 50 mL of a 10% (w/v) compound (C) solution of 50:50 (v/v) aqueous 1, 2-propylene glycol in a 100 mL glass jar and degassed for 15 minutes under reduced pressure (ca. 40 mm Hg) and purged with nitrogen gas aeration. The jar was capped and transferred into glove box with a nitrogen gas atmosphere with less than 0.2 percent oxygen gas (v/v) and a temperature of 55° C. and equilibrated on a shaker (180 rpm) for 90 minutes. The temperature of the suspension was then 55° C. The cap was replaced by a clear plastic cover, and the suspension was irradiated using 420 LEDs from the top having an intensity of 1.2 mW/cm$^2$ for 20 minutes while still being shaken. After irradiation, the lenses were removed and washed two times with deionized water and two times with borate buffered packing solution. The lenses were stored in vials. After one day of equilibration, the lenses were inspected and sterilized by autoclaving at 122° C. for 30 minutes. The lenses (4D) were equilibrated 3-4 days after sterilization, and then, the physical properties of the sterile lenses were measured as listed in Table 3.

TABLE 2

Formulation Components

| Component | Weight Percent |
|---|---|
| OH-mPDMS (n = 4) | 13 |
| OH-mPDMS (n = 15) | 49 |
| DMA | 21 |
| HEMA | 6 |
| PVP K90 | 7 |
| TEGDMA | 1.64 |
| Norbloc | 2 |
| Blue-HEMA | 0.02 |
| Omnirad 819 | 0.34 |
| Σ Components | 100 |

TABLE 3

Physical Properties

| Description | Lenses 4A | Lenses 4B | Lenses 4C | Lenses 4D |
|---|---|---|---|---|
| Zwitterionic Monomer | None | CBT | Compound (B) | Compound (C) |
| % GWG | 0 | 5.33 | 4.34 | 2.36 |
| % WC | 39 (0) | 47 (0) | 48 (1) | 43 (0) |
| Refractive Index | 1.4126 | 1.4037 | 1.4052 | 1.4079 |

Grafted Lenses 4D were round with acceptable circularity. Grafted lenses 4C were slightly out of round but acceptable. Grafted lenses 4B were completely distorted with wavy edges.

Example 5—Polymers

Preparation 1

50.0 grams (39.2 mmol) of tellurium powder was reacted with 14.4 mL of a 3.0 M methyl lithium solution (43.1 mmol) in anhydrous tetrahydrofuran to form a tellurolate intermediate, which was reacted with 8.82 grams (45.1 mmol) of ethyl α-bromoisobutyrate to form the organotellurium mediated living radical polymerization mediator, ethyl 2-methyl-2-methyltellanyl-propanoate (Te-Me). The reaction was performed with an ice bath for the metal exchange step. Following the addition of ethyl α-bromoisobutyrate, the reaction mixture was warmed and maintained at room temperature until the reaction was complete (about 2 hours). Thereafter, the tetrahydrofuran was removed at reduced pressure in a rotary evaporator. The crude product was vacuum distilled at 50-55° C. (1-2 mbar) to yield the organotellurium mediated living radical polymerization mediator, Te-Me, and characterized by proton nuclear magnetic resonance spectroscopy.

The following Examples 5A to 5D, and 6 are prophetic and serve to further illustrate the invention.

Example 5A 26.5 grams (100 mmol) Compound (A) and 578 milligrams (3.5 mmol) AIBN are added into a 1-liter reactor and dissolved in about 250 mL of 50:50 (v/v) aqueous methanol. The solution is degassed by bubbling nitrogen gas through the system for about 15 minutes at room temperature. The reaction mixture is heated at 60-62° C. under a nitrogen gas atmosphere for about 12 hours and then cooled to room temperature. The solvent is evaporated under reduced pressure. Acetone is added to the residue. The resulting mixture is heated to 62° C. for 12 hours with constant stirring; thereafter, the mixture is cooled to room temperature. Upon standing for two hours at room temperature, the insoluble solids settle. The acetone is decanted off and discarded. The crude product is rinsed for two additional hours in acetone at room temperature with stirring. The acetone is decanted off and discarded. The homopolymer is then vacuum dried at 60-65° C. to constant weight.

Example 5B 13.3 grams (50 mmol) Compound (A), 5.0 grams (50 mmol) DMA, and 578 milligrams (3.5 mmol) AIBN are added into a 1-liter reactor and dissolved in about 250 mL of 50:50 (v/v) aqueous methanol. The solution is degassed by bubbling nitrogen gas through the system for about 15 minutes at room temperature. The reaction mixture is heated at 60-62° C. under a nitrogen gas atmosphere for about 12 hours and then cooled to room temperature. The solvent is evaporated under reduced pressure. Acetone is added to the residue. The resulting mixture is heated to 62° C. for 12 hours with constant stirring; thereafter, the mixture is cooled to room temperature. Upon standing for two hours at room temperature, the insoluble solids settle. The acetone is decanted off and discarded. The crude product is rinsed for two additional hours in acetone at room temperature with stirring. The acetone is decanted off and discarded. The copolymer is then vacuum dried at 60-65° C. to constant weight.

Example 5C 13.3 grams (50 mmol) Compound (A), 5.0 grams (50 mmol) DMA, 907 milligrams (3.5 mmol) Te-Me, and 578 milligrams (3.5 mmol) AIBN are added into a 1-liter reactor and dissolved in about 250 mL of 50:50 (v/v) aqueous methanol. The solution is degassed by bubbling nitrogen gas through the system for about 15 minutes at room temperature. The reaction mixture is heated at 60-62° C. under a nitrogen gas atmosphere for about 12 hours and then cooled to room temperature. The solvent is evaporated under reduced pressure. Acetone is added to the residue. The resulting mixture is heated to 62° C. for 12 hours with constant stirring; thereafter, the mixture is cooled to room temperature. Upon standing for two hours at room temperature, the insoluble solids settle. The acetone is decanted off and discarded. The crude product is rinsed for two additional hours in acetone at room temperature with stirring. The acetone is decanted off and discarded. The copolymer is then vacuum dried at 60-65° C. to constant weight.

Example 5D 13.3 grams (50 mmol) Compound (A), 907 milligrams (3.5 mmol) Te-Me, and 578 milligrams (3.5 mmol) AIBN are added into a 1-liter reactor and dissolved in about 250 mL of 1-propanol. The solution is degassed by bubbling nitrogen gas through the system for about 15 minutes at room temperature. The reaction mixture is heated at 60-62° C. under a nitrogen gas atmosphere for about 3 hours. 13.0 grams (100 mmol) HEMA is dissolved in 30 mL of 1-propanol, degassed by bubbling nitrogen gas through the system for 15 minutes at room temperature, charged into the reaction vessel, and heated at 70-72° C. with constant stirring for about 6 hours. Finally, 13.3 grams (50 mmol) Compound (A) is dissolved in 30 mL of 1-propanol, degassed by bubbling nitrogen gas through the system for 15 minutes at room temperature, charged into the reaction vessel, and heated at 60-62° C. with constant stirring for about 4 hours.

The volatile components of the reaction mixture are removed under reduced pressure in a rotary evaporator. The crude product is re-dissolved in 400 mL of toluene at 60° C. and cooled down to room temperature. The mixed solvent system is removed by rotary evaporation to yield a crude product free of 1-propanol. The crude product contains a methyl tellurium end group. To remove this organometallic end group, the crude product is dissolved in 250 mL toluene containing an amount of TEMPO representing 3.5 times the theoretical molar amount of methyl tellurium. This solution is heated at 88° C. for 4 hours. The reaction mixture is cool down to room temperature, and then the volatile components are evaporated at 60-65° C. on a rotary evaporator. The residue is dissolved in 1000 mL of acetonitrile at 72° C. for 30 minutes, forming a cloudy solution. The cloudy solution was cooled to room temperature. After standing for some time allowing the insoluble solids to settle, the solvent is decanted off. The triblock copolymer is isolated by evaporating off the acetonitrile and vacuum drying at 60-65° C. to constant weight. The triblock copolymer may be further purified by precipitation or extraction.

Example 6—Hydrogel Contact Lenses

A reactive monomer mixture is prepared composed of 50 weight percent of the formulation listed in Table 4 and 50 weight percent of the diluent BAGE. The reactive monomer mixture is filtered through a 3 μm filter using a stainless-steel syringe under pressure and subsequently degassed under reduce pressure for about thirty minutes. In a glove box with a nitrogen gas atmosphere and less than 0.2 percent oxygen gas (v/v), about 75-100 μL of the reactive mixture are dosed using an Eppendorf pipet at room temperature into the front curve mold made of Zeonor. The base curve mold made of a 55:45 (w/w) blend of Zeonor and polypropylene is then placed onto the front curve mold. The molds are equilibrated for a minimum of twelve hours in the glove box prior to dosing. A plate containing about four pallets, each pallet containing eight lens mold assemblies, is transferred into an adjacent glove box maintained at about 62° C., and the lenses are cured from the top for 5 minutes using TL03 lights having intensity of 4.5 mW/cm$^2$.

The lenses are manually de-molded with most lenses adhering to the front curve mold and released by suspending the lenses in 80 percent isopropanol for about one or two hours (about one lens per 15 mL), sometimes overnight, followed by washing two times with 80 percent isopropanol, two times with deionized water, two times with borate buffered packing solution, and finally stored in borate buffered packing solution in vials. After one day of equilibration, the lenses were inspected and sterilized by autoclaving at 122° C. for 30 minutes.

TABLE 4

Formulation Components

| Component | Weight Percent |
|---|---|
| HEMA | 94 |
| Compound (A) | 3 |
| EGDMA | 1 |
| Norbloc | 1 |
| Blue-HEMA | 0.02 |

TABLE 4-continued

Formulation Components

| Component | Weight Percent |
|---|---|
| Omnirad 1700 | 0.98 |
| Σ Components | 100 |

We claim:

1. A zwitterionic polymerizable compound of formula I:

(I)

wherein $R^1$, $R^2$, and $R^3$ are independently H, alkyl, cycloalkyl, phenyl or benzyl;
$L^1$ and $L^2$ are each independently alkylene; and
$P_g$ is a polymerizable group.

2. The compound of claim 1 wherein $R^1$ is H or $C_1$-$C_6$ alkyl.

3. The compound of claim 1 wherein $R^2$ is H.

4. The compound of claim 1 wherein $R^3$ is H.

5. The compound of claim 1 wherein $P_g$ comprises styryl, vinyl carbonate, vinyl ether, vinyl carbamate, N-vinyl lactam, N-vinylamide, (meth)acrylate, or (meth)acrylamide.

6. The compound of claim 1 that is:
3-(1-(3-methacrylamidopropyl)-1H-imidazol-3-ium-3-yl)propanoate;
3-(1-(3-methacrylamidopropyl)-2-methyl-1H-imidazol-3-ium-3-yl)propanoate; or
4-(1-(3-methacrylamidopropyl)-2-methyl-1H-imidazol-3-ium-3-yl)butanoate.

7. An ophthalmic device comprising a polymer derived from a zwitterionic polymerizable compound of formula I:

(I)

wherein $R^1$, $R^2$, and $R^3$ are independently H, alkyl, cycloalkyl, phenyl or benzyl; $L^1$ and $L^2$ are each independently a linking group; and $P_g$ is a polymerizable group.

8. The ophthalmic device of claim 7 wherein the polymer is contained in or is coated on the device.

9. The ophthalmic device of claim 7 wherein the polymer comprises a free radical reaction product of the compound and one or more monomers suitable for making the ophthalmic device.

10. The ophthalmic device of claim 9 wherein the monomer suitable for making the ophthalmic device is selected from a hydrophilic component, a hydrophobic component, a silicone-containing component, and mixtures of two or more thereof.

11. The ophthalmic device of claim 7 that is an intraocular lens or a soft contact lens.

12. The ophthalmic device of claim 11 that is a hydrogel contact lens.

13. A blister package including an ophthalmic device and a packaging solution, wherein the packaging solution comprises a polymer derived from a polymerizable zwitterion compound of formula I:

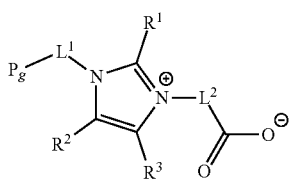

(I)

wherein $R^1$, $R^2$, and $R^3$ are independently H, alkyl, cycloalkyl, phenyl or benzyl; $L^1$ and $L^2$ are each independently a linking group; and $P_g$ is a polymerizable group.

14. The ophthalmic device of claim 7 wherein $R^1$ is H or $C_1$-$C_6$ alkyl.

15. The ophthalmic device of claim 7 wherein $R^2$ is H and $R^3$ is H.

16. The ophthalmic device of claim 7 wherein $L^1$ and $L^2$ are independently alkylene.

17. The ophthalmic device of claim 7 wherein $P_g$ comprises styryl, vinyl carbonate, vinyl ether, vinyl carbamate, N-vinyl lactam, N-vinylamide, (meth)acrylate, or (meth)acrylamide.

18. The ophthalmic device of claim 7 wherein the zwitterionic polymerizable compound is:
- 3-(1-(3-methacrylamidopropyl)-1H-imidazol-3-ium-3-yl)propanoate;
- 3-(1-(3-methacrylamidopropyl)-2-methyl-1H-imidazol-3-ium-3-yl)propanoate; or
- 4-(1-(3-methacrylamidopropyl)-2-methyl-1H-imidazol-3-ium-3-yl)butanoate.

* * * * *